US006527790B2

United States Patent
Chien et al.

(10) Patent No.: US 6,527,790 B2
(45) Date of Patent: Mar. 4, 2003

(54) INTRAVASCULAR BALLOON CATHETER FOR EMBOLIC COIL DELIVERY

(75) Inventors: Thomas Yung-Hui Chien, San Jose, CA (US); Greg P. Welsh, San Jose, CA (US); Huey Quoc Chan, San Jose, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 176 days.

(21) Appl. No.: 09/732,476

(22) Filed: Dec. 7, 2000

(65) Prior Publication Data

US 2002/0072763 A1 Jun. 13, 2002

(51) Int. Cl.[7] .............................................. A61M 29/02
(52) U.S. Cl. ........................................ 606/194; 606/195
(58) Field of Search ................................. 606/191, 192, 606/194, 195, 200

(56) References Cited

U.S. PATENT DOCUMENTS

| | | | |
|---|---|---|---|
| 4,606,347 A | 8/1986 | Fogarty et al. ............. 128/344 |
| 4,610,662 A | 9/1986 | Weikl et al. ................... 604/53 |
| 4,636,195 A | 1/1987 | Wolinsky ...................... 604/53 |
| 4,813,934 A | 3/1989 | Engelson et al. .............. 604/99 |
| 5,122,136 A | 6/1992 | Guglielmi et al. ............ 606/32 |
| 5,209,728 A | 5/1993 | Kraus et al. ................... 604/96 |
| 5,304,198 A | 4/1994 | Samson ....................... 604/194 |
| 5,354,295 A | 10/1994 | Guglielmi et al. ............ 606/32 |
| 5,540,680 A | 7/1996 | Guglielmi et al. ............. 606/32 |
| 5,569,245 A | 10/1996 | Guglielmi et al. ............. 606/49 |
| 5,588,961 A | 12/1996 | Leone et al. ................... 604/21 |
| 5,645,529 A | 7/1997 | Fagan et al. ................. 604/101 |
| 5,662,609 A | 9/1997 | Slepian ........................ 604/101 |
| 5,718,683 A * | 2/1998 | Ressemann et al. ...... 604/96.01 |
| 5,795,331 A * | 8/1998 | Cragg et al. ........... 604/103.01 |
| 5,928,260 A * | 7/1999 | Chin et al. ................... 604/107 |
| 5,976,131 A | 11/1999 | Guglielmi et al. ............. 606/49 |
| 6,074,407 A * | 6/2000 | Levine et al. ................ 606/194 |

* cited by examiner

Primary Examiner—John J. Calvert
Assistant Examiner—Shaun R Hurley
(74) Attorney, Agent, or Firm—Crompton, Seager & Tufte, LLC

(57) ABSTRACT

Improved intravascular balloon catheters for the delivery of embolic agents and devices such as coils to wide-neck aneurysms. In one embodiment, the present invention provides a balloon catheter having a combined guide wire/delivery lumen and a lateral delivery hole. The balloon may comprise a multi-lobed design with the delivery hole disposed between adjacent balloon lobes. The balloon catheter preferably includes a diversion member disposed in the combined lumen to cause the embolic device to divert from the combined lumen, through the delivery hole, and into the wide-neck aneurysm. In another embodiment, the present invention provides a balloon catheter having a shaft including a shaft tube and a co-extending embolic delivery tube. The delivery tube terminates proximal of the distal end of the shaft tube for added flexibility, and the balloon may inflate eccentrically to push the distal opening of the delivery lumen adjacent the opening of the wide-neck aneurysm.

15 Claims, 3 Drawing Sheets

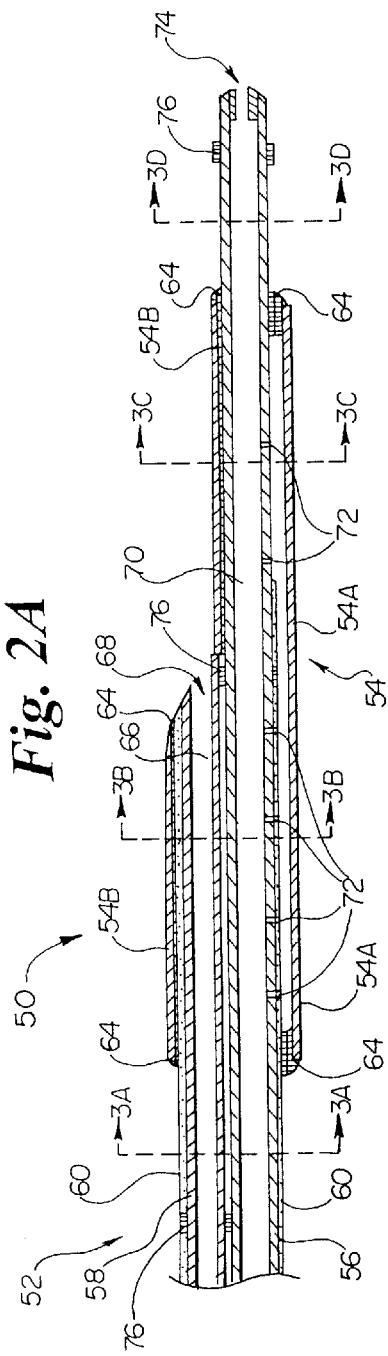
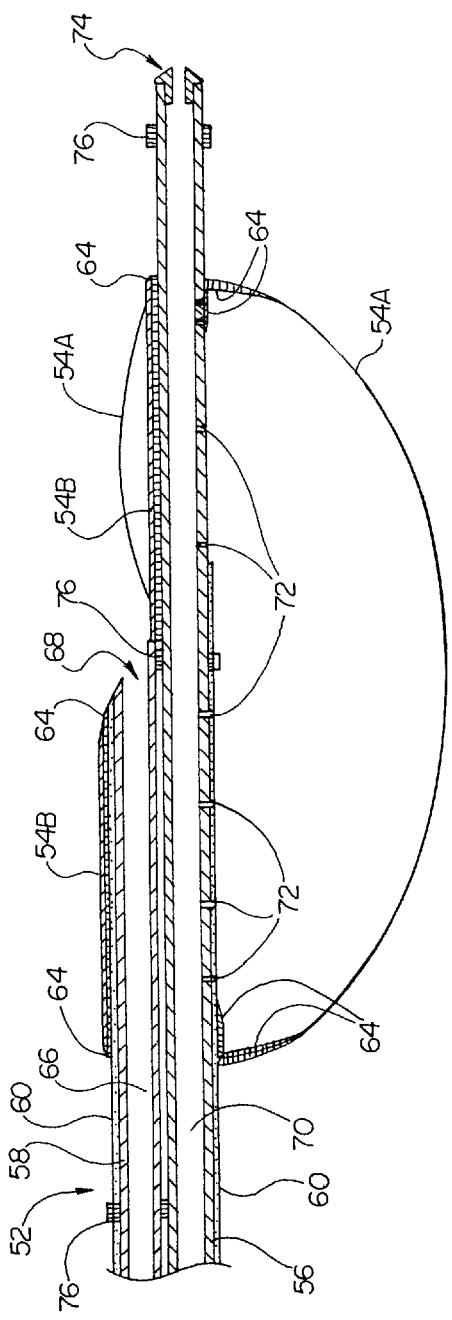
Fig. 2A
Fig. 2B

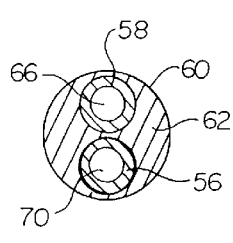 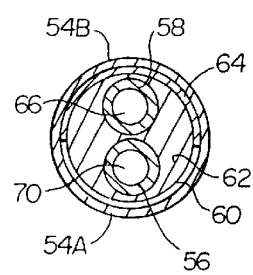 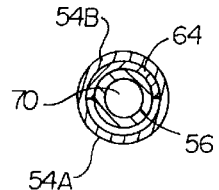 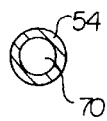
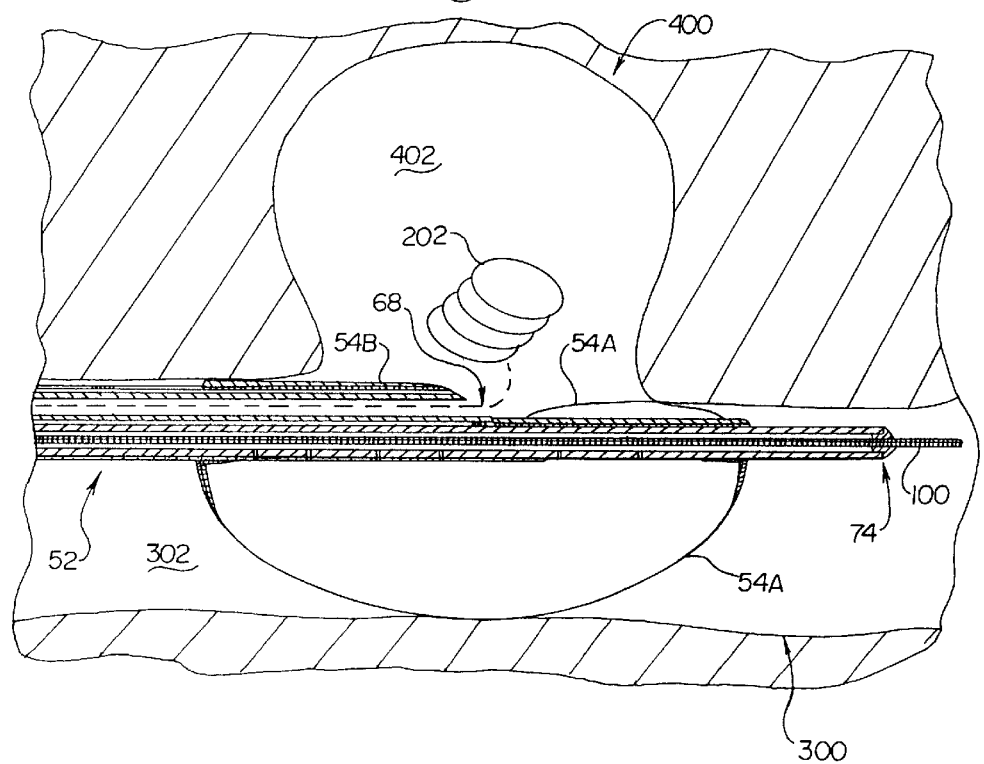

US 6,527,790 B2

INTRAVASCULAR BALLOON CATHETER FOR EMBOLIC COIL DELIVERY

FIELD OF THE INVENTION

The present invention generally relates to intravascular balloon catheters. More specifically, the present invention relates to intravascular balloon catheters for the delivery of embolic devices and agents to aneurysms.

BACKGROUND OF THE INVENTION

Embolic devices and agents have been proposed for the treatment of vascular diseases and malformations requiring the formation of thrombus. For example, embolic coils have been proposed for the treatment of aneurysms. A currently preferred method of deploying an embolic coil to an aneurysm utilizes an electrolytically detachable guide wire tip or coil commercially available under the trade name GDC (Guglielmi Detachable Coil) available from Boston Scientific Corporation. The GDC system and method of use is substantially described in U.S. Pat. No. 5,354,295 to Guglielmi et al., and other related patents and patent applications.

Some types of vascular aneurysms have a relatively large opening between the native vascular lumen and the cavity of the aneurysm. For example, aneurysms which have an opening that is the same size or larger than the cavity may be referred to as wide-neck aneurysms. Wide-neck aneurysms are typically difficult to embolize with embolic devices and agents because the embolic material has a tendency to fall out or otherwise exit the aneurysm during delivery. In the case of embolic coils, wide-neck aneurysms are particularly problematic when the neck of the aneurysm is as large or larger than the expanded size of the embolic coil.

To address this problem, a separate balloon catheter is often utilized to block the neck of the aneurysm during embolic coil delivery to prevent the coil from exiting or protruding out of the aneurysm. Although not intended for use in the treatment of wideneck aneurisms, U.S. Pat. No. 5,795,331 to Craigg et al., disclose a method and apparatus for delivering an occluding agent into an aneurysm or branch vessel utilizing a balloon catheter. The balloon catheter disclosed by Craigg et al., includes an elongate shaft having a guide wire lumen and one or more delivery lumens for the delivery of an embolic agent. A balloon is disposed about the distal end of the elongate shaft for inflation in the vessel adjacent the aneurysm such that the exit port of the delivery lumen is disposed adjacent to the opening of the aneurysm. In each of the embodiments disclosed by Craigg et al., the portion of the elongate shaft which defines the delivery lumen extends distal of the balloon thereby unnecessarily adding stiffness to the distal end of the catheter and compromising flexibility and navigability thereof. In addition, all of the embodiments disclosed by Craigg et al. utilize delivery lumens which are separate from the guide wire lumen thereby unnecessarily increasing the overall profile of the catheter in situations where the some of the lumens may be combined.

SUMMARY OF THE INVENTION

To address these problems, the present invention provides improved intravascular balloon catheters for the delivery of embolic devices and agents to wide-neck aneurysms. In one embodiment, the present invention provides a balloon catheter having a combined guide wire/delivery lumen and a lateral delivery hole for an embolic device to pass from the combined lumen into the wide-neck aneurysm. The combined lumen reduces the profile of the balloon catheter to provide improved trackability, particularly in small diameter tortuous vasculature. The balloon may comprise a multi-lobed design with the delivery hole disposed between adjacent balloon lobes. The balloon catheter preferably includes a diversion member disposed in the combined lumen to cause the embolic device to divert from the combined lumen, through the delivery hole, and into the opening of the wide-neck aneurysm.

In another embodiment, the present invention provides a balloon catheter including a shaft having a shaft tube and a co-extending delivery tube. The delivery tube includes a distal opening for the delivery of an embolic agent or device such as a coil. The delivery tube terminates proximal of the distal end of the shaft tube for added flexibility and improved trackability. An inflatable balloon is connected to the distal end of the shaft, and the balloon may inflate eccentrically about the distal end thereof. The eccentric balloon pushes the distal opening of the delivery lumen adjacent the opening of the wide-neck aneurysm. The balloon catheter may include a distal guide wire seal to accommodate a single lumen design.

BRIEF DESCRIPTION OF THE DRAWINGS

FIGS. 2A and 2B illustrate longitudinal cross sectional views of a distal portion of a balloon catheter for embolic device delivery in accordance with another embodiment of the present invention;

FIGS. 3A–3D illustrate cross sectional views taken along lines 3A—3A, 3B—3B, 3C—3C and 3D—3D, respectively, in FIG. 2A; and FIG. 4 illustrates the delivery of an embolic coil into a wide-neck aneurysm utilizing the catheter shown in FIGS. 2A and 2B.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1A:
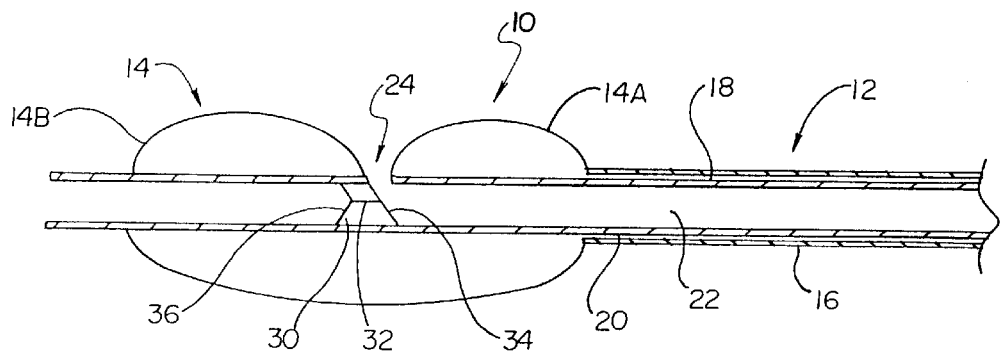
FIGS. 1A–1C illustrate longitudinal cross sectional views of a distal portion of a balloon catheter for embolic device delivery in accordance with an embodiment of the present invention.
Figure 1B:
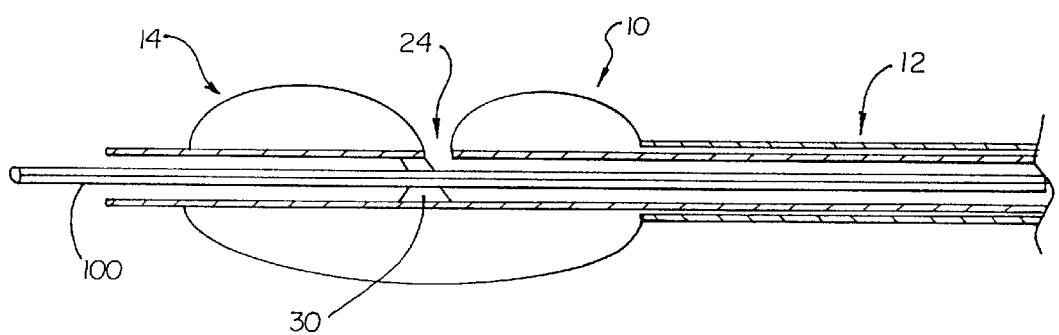
Figure 1C:
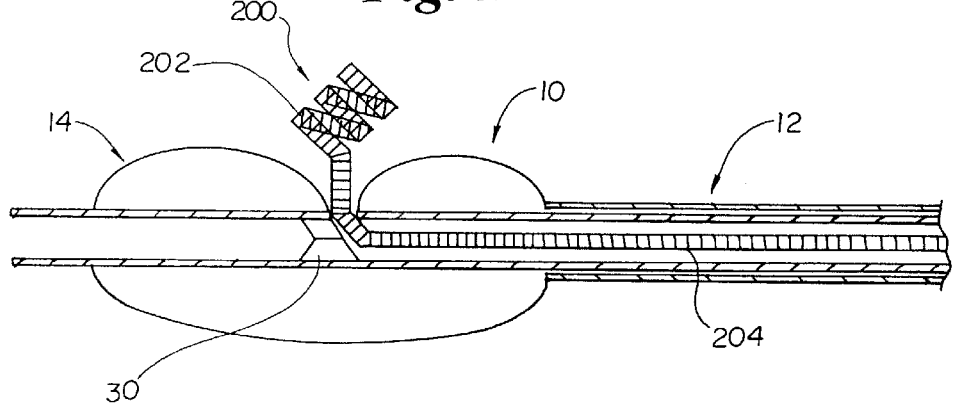

Refer now to FIG. 1A which illustrates a longitudinal cross sectional view of a distal portion of a balloon catheter 10 for the delivery of an embolic device such as a coil to a wide-neck aneurysm. FIG. 1A illustrates the balloon catheter 10 in the inflated state, FIG. 1B illustrates the balloon catheter 10 with a guide wire 100 disposed therein, and FIG. 1C illustrates the balloon catheter 10 with an embolic device 200 disposed therein.

Although described with reference to an embolic coil, those skilled in the art will recognize that the present invention may be utilized to deliver other mechanical embolic devices in addition to chemical embolic agents. Furthermore, although described with reference to wide-neck aneurysms, the present invention may be utilized in the treatment of other vascular diseases and malformations calling for the occlusion of a vascular lumen, opening or cavity, such as may occur in, for example, arteries, veins, aneurysms, vascular shunts, arteriovenous fistulas, etc.

The balloon catheter 10 includes an elongate shaft 12 having a proximal end and a distal end. An inflatable balloon 14 is connected to the distal end of the elongate shaft 12. A manifold (not shown) is connected to the proximal end of the elongate shaft 12 to facilitate connection to an inflation device for inflating/deflating the balloon 14, and to facilitate insertion of the guide wire 100 and/or the embolic device 200. The elongate shaft 12 and the balloon 14 may comprise conventional designs having conventional dimensions and materials except as described herein.

The balloon catheter 10 is adapted to be used in combination with a guide wire 100. The balloon catheter 10 may comprise a fixed-wire type balloon catheter or an over-the-wire type balloon catheter as shown. Over-the-wire type of embodiments of the balloon catheter 10 may incorporate a single lumen design or a multi-lumen design (e.g., side-by-side dual lumen, coaxial lumens, etc.) as shown. In the coaxial multi-lumen design shown, the elongate shaft 12 includes an inner tube 18 disposed in an outer tube 16. The inner tube 18 is connected to the distal end of the inflatable balloon 14 and defines a combined guide wire/delivery lumen 22 therein. The outer tube 16 is connected to the proximal end of the inflatable balloon 14 and defines an annular inflation lumen 20 therein. The inflation lumen 20 is in fluid communication with the interior of the balloon 14 for inflation and deflation thereof.

In the single lumen design (not shown), the outer tube 16 may be eliminated by connecting both the proximal and distal ends of the inflatable balloon 14 to the inner tube 18 and by providing an inflation port (not shown) through the wall of the inner tube 18 to establish fluid communication between the combined lumen 22 and the interior of the balloon 14. To facilitate inflation and deflation of the balloon 14, a guide wire seal (not shown) may be incorporated into the distal end of the inner tube 18 to provide a fluid tight seal about the guide wire 100 disposed therein. The guide wire seal may comprise a gap-type seal or an interference-type seal, both of which inhibit the loss of inflation therethrough and allow free longitudinal and rotational movement of the guide wire 100 therein.

The balloon catheter 10 includes a delivery hole 24 extending through the wall of the inner tube 18. The delivery hole 24 allows for the passage of the embolic device 200 from the combined lumen 22 into the aneurysm as illustrated in FIG. 1C. The embolic device 200 may comprise, for example, a GDC embolic device as disclosed in U.S. Pat. No. 5,122,136 to Guglielmi et al., the entire disclosure of which is hereby incorporated by reference. The embolic device 200 generally includes a distally disposed detachable coil 202 and a proximal delivery shaft 204.

With the delivery hole 24 disposed adjacent the balloon 14, the balloon 14 must be arranged to provide a delivery path from the combined lumen 22 to the exterior of the catheter 10 adjacent the opening to the aneurysm. To accommodate the delivery path, the inflatable balloon 14 may incorporate two or more inflation lobes 14A/14B between which the delivery hole 24 is disposed. The balloon lobes 14A/14B may extend around the entire circumference of the inner tube 18 or may extend around only a portion thereof as shown. To define the balloon lobes 14A/14B, half of the circumference of the mid portion of the balloon 14 may be connected to the inner tube 18. This may be accomplished, for example, by utilizing a conventional single lobe balloon and adhesively tacking a mid portion of the balloon 14 to the outer surface of the inner tube 18. The delivery hole 24 may then be formed through the mid portion of the balloon 14 and the inner tube 18 connected thereto.

The balloon catheter 10 may include a diversion member 30 disposed in the combined lumen 22 to facilitate diversion of the embolic device 200 through the delivery hole 24. Preferably, the diversion member 30 fills the entire cross sectional area of the lumen 22. The diversion member 30 may include a guide wire passage 32 in the form of a hole, slot, slit, etc. to allow the guide wire 100 to be slidably inserted therethrough. The diversion member 30 may include a proximal inclined face 34 and a distal concave face 36. The proximal inclined face 34 preferentially directs the embolic device 200 from the combined lumen 22 through the delivery hole 24. The concave distal face 36 preferentially directs the proximal end of the guide wire 100 through the guide wire passage 32 such that the guide wire 100 may be easily back-loaded into the catheter 10.

In preparing the balloon catheter 10 for use, the combined lumen 22 is flushed and the inflation lumen 20 is purged of all air utilizing a syringe connected to the manifold (not shown) at the proximal end of the shaft 12. The guide wire 100 is then back-loaded into the distal end of the combined lumen 22 such that the proximal end of the guide wire 100 engages the concave distal face 36 of the diversion member 30. The proximal end of the guide wire 100 is advanced in the proximal direction through the guide wire passage 32 and through the remainder of the elongate shaft 12, until the distal end of the guide wire 100 is adjacent the distal end of the balloon catheter 10.

To position the balloon catheter in the patient's vascular system, an appropriate guiding catheter (not shown) may be placed in the vascular lumen using conventional techniques. The guide wire 100 and the balloon catheter 10 are then inserted into the guide catheter until the distal tip of the catheter 10 reaches the distal end of the guide catheter. The balloon catheter 10 and guide wire 100 are then alternatively advanced until the balloon 14 is positioned adjacent the aneurysm to be treated. Although shown in the inflated state, the balloon 14 is preferably deflated during navigation through the patient's vascular system to the desired treatment site. The position of the balloon 14 relative to the aneurysm may be established using conventional radiographic techniques in combination with radiopaque markers (not shown) disposed on the distal end of the catheter 10 adjacent the balloon 14.

When the balloon 14 is positioned adjacent the aneurysm to be occluded, the catheter 10 is rotated, if necessary, until the delivery hole 24 is aligned with the neck of the aneurysm. The balloon 14 is then slowly inflated using the inflation device until the balloon lobes 14A/14B come into contact with the portion of the vascular wall defining the neck of the aneurysm, and the opposite portion of the balloon 14 pushes the delivery hole 24 into close proximity to the opening of the aneurysm. Once inflated, the guide wire 100 may be withdrawn from the catheter 10 in the proximal direction thereby allowing the guide wire passage 32 in the diversion member 30 to close.

The embolic device 200 is then advanced through the combined lumen 22 and diverted into the delivery hole 24 by virtue of diversion member 30, until the detachable coil portion 202 is disposed within the aneurysm. The detachment mechanism is activated to release the coil 202 from the shaft 204 of the embolic device 200. With the detached embolic coil 202 disposed in the aneurysm, the balloon 14 is deflated and the catheter 10 is withdrawn from the patient's vascular system. In some instances, it may be desirable to maintain the balloon 14 in the inflated state after the embolic coil 202 is deployed in order to allow thrombus formation in the aneurysm to hold the coil 202 therein.

Refer now to FIGS. 2A and 2B which illustrate longitudinal cross sectional views of a distal portion of a balloon catheter 50 in accordance with an alternative embodiment of the present invention. FIG. 2A illustrates the balloon catheter 50 in the deflated state, and FIG. 2B illustrates the balloon catheter 50 in the inflated state. Except as described herein, the balloon catheter 50 is substantially the same in terms of design, function and use as balloon catheter 10 described previously.

Balloon catheter 50 includes an elongate shaft 52 having a proximal end and a distal end. A manifold (not shown) is connected to the proximal end of the elongate shaft 52. An inflatable balloon 54 is connected to the distal end of the elongate shaft 52. Radiopaque marker bands 76 may be disposed adjacent the proximal, mid, and distal portions of the inflatable balloon 54 to facilitate radiographic placement thereof.

The elongate shaft 52 includes a shaft tube 56 and a delivery tube 58. The distal end of the delivery tube 58 terminates proximal of the distal end of the shaft tube 56 to impart additional flexibility to the distal end of the elongate shaft 52. An outer sleeve member 60 covers a majority of the length of the shaft tube 56 and delivery tube 58. As best seen in FIG. 3A, a filler material 62 is disposed between the outer sleeve 60 and the tubes 56/58.

The inflatable balloon 54 includes an inflatable portion 54A and a non-inflatable portion 54B. The inflatable portion 54A is connected at its proximal and distal ends to the shaft tube 56. The non-inflatable portion 54B is connected along its entire length to the shaft tube 56 and delivery tube 58 as shown. The inflatable balloon 54 may be connected to the elongate shaft 52 utilizing an adhesive 64 or other connection means known to those skilled in the art. With this arrangement, the balloon 54 inflates eccentrically about the distal portion of the elongate shaft 52 as best seen in FIG. 2B. Those skilled in the art will recognize that the eccentric balloon arrangement may be provided by connecting the balloon 54 to the elongate shaft 52 as shown, or by other suitable means such as disclosed in U.S. Pat. No. 5,718,683 to Ressemann et al., the disclosure of which is hereby incorporated by reference.

The delivery tube 58 defines a delivery lumen 66 and a distal delivery hole 68. The shaft tube 56 defines a common guide wire/inflation lumen 70 which is in fluid communication with the interior of the balloon 54 by way of a plurality of inflation ports 72. Because the elongate shaft 52 utilizes a common guide wire/inflation lumen 70, a guide wire seal 74 is provided at the distal end of the shaft tube 56 to provide a fluid tight seal about the guide wire 100 disposed therein. As mentioned previously, the guide wire seal 74 may comprise a gap-type seal or an interference-type seal, both of which provide a fluid tight seal about the guide wire 100 disposed therein and permit relative longitudinal and rotational movement thereof.

In preparing the balloon catheter 50 for use, the common guide wire/inflation lumen 70 is flushed and the balloon 54 is partially inflated to purge the system of air utilizing an inflation device such as a syringe connected to the manifold (not shown). The guide wire 100 is then advanced through the common guide wire/inflation lumen 70 until the distal end of the guide wire 100 exits the distal end of the guide wire seal 74. The inflation device is then used to partially inflate the balloon 54 to inspect it for surface abnormalities and/or air bubbles. If air bubbles remain in the balloon 54 or lumen 70, the guide wire 100 may be pulled back from the guide wire seal 74 and additional inflation fluid may be flushed into the common lumen 70 and balloon 54 to purge all air bubbles therefrom.

With reference to FIG. 4, the balloon catheter 50 may be positioned in the patient's vascular system adjacent an aneurysm 400 utilizing an appropriate guiding catheter (not shown) placed in the vascular lumen using conventional techniques. The guide wire 100 and balloon catheter 50 are advanced through the guide catheter and navigated through the patient's vascular system as described previously until the delivery hole 68 is positioned in the center of the aneurysm 400 as seen in FIG. 4. The position of the balloon 54 and the delivery hole 68 may be confirmed utilizing conventional radiographic techniques in combination with radiopaque markers 76.

With the balloon 54 and the delivery hole 68 centered in the opening of the aneurysm 400, the balloon 54 is inflated thereby occluding the native lumen 302 of the vessel 300 and pushing the delivery hole 68 immediately adjacent the opening of the aneurysm 400. Prior to inflating the balloon 54, the catheter 50 may be rotated, if necessary, until the delivery hole 68 is adjacent the opening to the aneurysm 400.

Once inflated, the embolic device 200 is advanced through the delivery lumen 66 until the detachable coil portion 202 is disposed within the cavity 402 of the aneurysm 400. The detachment mechanism is then activated to release the coil 202. As mentioned previously, it may be desirable to maintain the balloon 54 in the inflated state after the detachable coil 202 is deployed in the cavity 402 in order to allow thrombus formation to hold the coil 202 therein. After the coil 202 is deployed and retained in the aneurysm cavity 402, the balloon 54 is deflated and the catheter 50 is withdrawn from the patient's vascular system.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular balloon catheter for the delivery of an embolic device to an aneurysm, the balloon catheter comprising:

an elongate shaft having a proximal end, a distal end, an inflation lumen extending therethrough and a combined guide wire/delivery lumen extending therethrough;

an inflatable balloon connected to the distal end of the elongate shaft; and an embolic device delivery hole extending through a wall of the elongate shaft, the delivery hole providing a delivery path from the combined lumen to the aneurysm.

2. An intravascular balloon catheter as in claim 1, wherein the balloon defines a plurality of balloon lobes and wherein the delivery hole extends through the wall of the elongate shaft between the plurality of balloon lobes.

3. An intravascular balloon catheter as in claim 2, further comprising a diversion member disposed in the combined lumen, the diversion member causing an embolic coil advanced through at least a part of the combined lumen to divert from the combined lumen into the delivery hole.

4. An intravascular balloon catheter as in claim 3, wherein the diversion member includes a guide wire passage extending therethrough.

5. An intravascular balloon catheter as in claim 4, wherein the guide wire passage is normally closed.

6. An intravascular balloon catheter as in claim 5, wherein the diversion member has a inclined proximal face.

7. An intravascular balloon catheter as in claim 6, wherein the diversion member has a concave distal face.

8. An intravascular balloon catheter for the delivery of an embolic device to an aneurysm, the balloon catheter comprising:
   an elongate shaft having a proximal end, a distal end, an inflation lumen extending therethrough and a combined guide wire/delivery lumen extending therethrough;
   an inflatable balloon connected to the distal end of the elongate shaft;
   an embolic device delivery hole extending through a wall of the elongate shaft adjacent the distal end of the shaft, the hole providing a delivery path from the combined lumen to the aneurysm; and
   a diversion member disposed in the combined lumen, the diversion member causing the embolic device to divert from the combined lumen into the delivery hole.

9. An intravascular balloon catheter as in claim 8, wherein the diversion member includes a guide wire passage extending therethrough.

10. An intravascular balloon catheter as in claim 9, wherein the guide wire passage is normally closed.

11. An intravascular balloon catheter as in claim 8, wherein the diversion member has a inclined proximal face.

12. An intravascular balloon catheter as in claim 8, wherein the diversion member has a concave distal face.

13. An intravascular balloon catheter for the delivery of an embolic device to an aneurysm, the balloon catheter comprising:
   an elongate shaft including a shaft tube and a co-extending delivery tube, the shaft tube having a proximal end, a distal end, and an inflation lumen extending therethrough, the delivery tube having a proximal end, a distal end, and an embolic delivery lumen extending therethrough, the distal end of the delivery tube disposed proximal of the distal end of the shaft tube; and
   an inflatable balloon connected to the distal end of the elongate shaft.

14. An intravascular balloon catheter as in claim 13, wherein the balloon inflates eccentrically about the distal end of the shaft.

15. An intravascular balloon catheter as in claim 14, further comprising a guide wire seal connected to the distal end of the elongate shaft distal of the balloon.

* * * * *

UNITED STATES PATENT AND TRADEMARK OFFICE
CERTIFICATE OF CORRECTION

PATENT NO.   : 6,527,790 B2
DATED        : March 4, 2003
INVENTOR(S)  : Thomas Yung-Hui Chien et al.

It is certified that error appears in the above-identified patent and that said Letters Patent is hereby corrected as shown below:

Column 5,
Line 8, delete "S0" and insert therefor -- 50 --.

Column 6,
Lines 60 and 62, delete "plurality of" and insert therefor -- first and second --.

Signed and Sealed this

Eighteenth Day of November, 2003

JAMES E. ROGAN
*Director of the United States Patent and Trademark Office*